United States Patent [19]

Abbate et al.

[11] Patent Number: 5,388,373
[45] Date of Patent: Feb. 14, 1995

[54] APPARATUS FOR APPLYING A CUTTING EDGE TO A NEEDLE

[75] Inventors: Richard Abbate, Wallingford; Stephen T. Cassidy, West Haven, both of Conn.

[73] Assignee: United States Surgical Corporation, Norwalk, Conn.

[21] Appl. No.: 959,326

[22] Filed: Oct. 9, 1992

[51] Int. Cl.⁶ .............................................. B24B 19/16
[52] U.S. Cl. ..................................... 451/65; 451/306
[58] Field of Search ................ 51/3, 328, 135 R, 144, 51/148, 147, 227 H

[56] References Cited

U.S. PATENT DOCUMENTS

| | | | |
|---|---|---|---|
| 160,686 | 3/1875 | Kingman | 51/217 R |
| 279,075 | 6/1883 | Berry | 51/327 |
| 2,215,752 | 9/1940 | Enya . | |
| 2,353,683 | 7/1944 | Martines | 51/328 |
| 2,452,205 | 10/1948 | Newton | 51/148 |
| 2,838,883 | 6/1958 | Hall | 51/227 H |
| 3,539,314 | 11/1970 | Rockefeller et al. . | |
| 4,063,906 | 12/1977 | Wetzels | 51/289 R |
| 4,112,625 | 9/1978 | Wetzels | 51/33 W |
| 4,173,100 | 11/1979 | MacBroom, Jr. | 51/227 H |
| 4,216,628 | 8/1980 | Wada | 51/227 H |
| 4,441,280 | 4/1984 | Wetzels et al. | 51/103 R |
| 5,155,943 | 10/1992 | Matsutani et al. | 51/328 |

FOREIGN PATENT DOCUMENTS

| | | |
|---|---|---|
| 0282440 | 9/1988 | European Pat. Off. . |
| 4304684 | 9/1993 | Germany . |
| 2006063 | 5/1979 | United Kingdom . |

OTHER PUBLICATIONS

European Search Report.
The Automatic Point Grinding Machine SCHUMAG Catalog Feb. 1988.

*Primary Examiner*—Robert A. Rose

[57] ABSTRACT

An apparatus for applying a cutting edge on surgical needles having at least one abrading device and a needle holding mechanism. The abrading device includes an abrasive member such as a rotatable abrasive belt or grinding wheel. The needle holding mechanism is positioned for selectively engaging an end of at least one needle with the abrading device to provide a cutting edge on the needle.

32 Claims, 8 Drawing Sheets

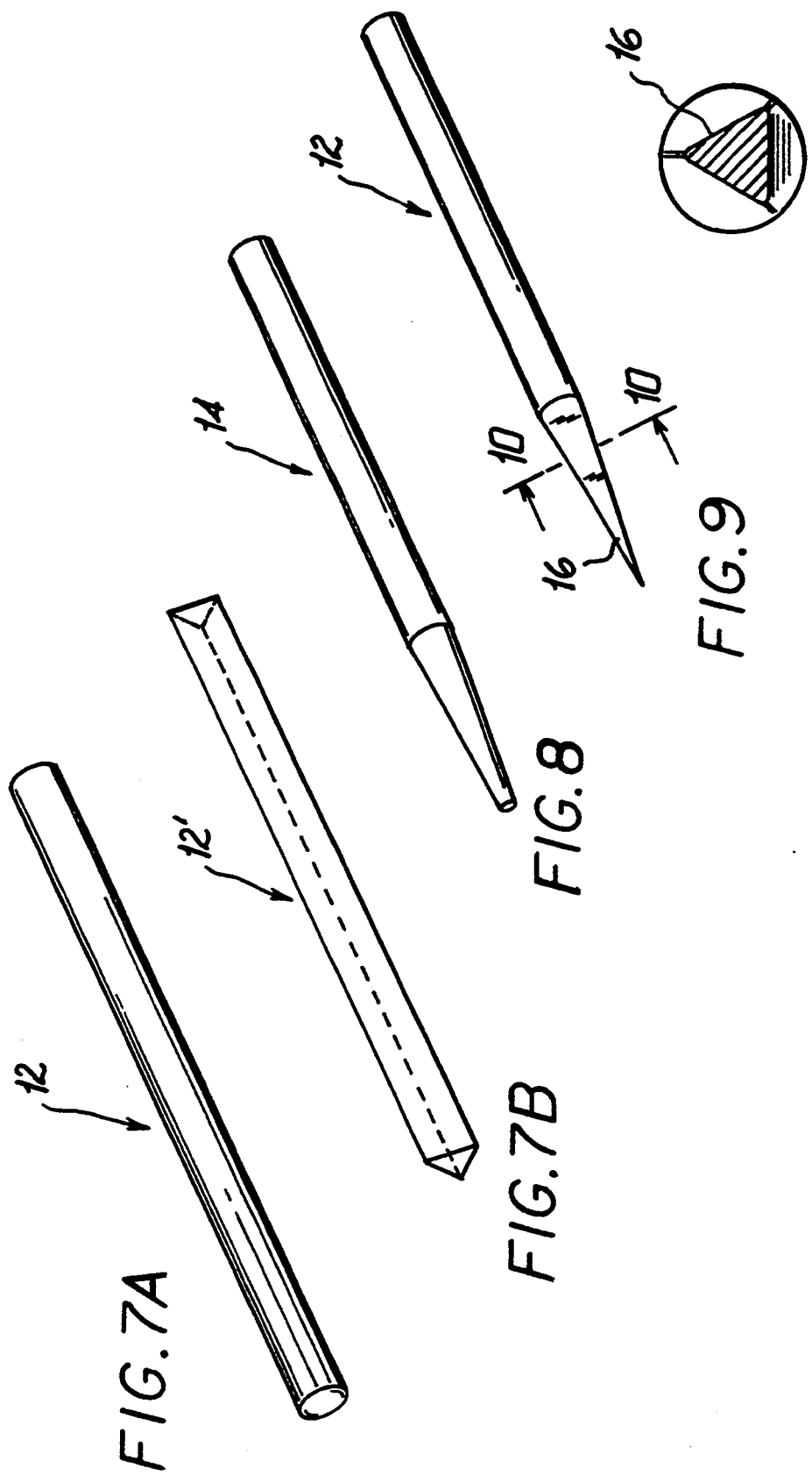

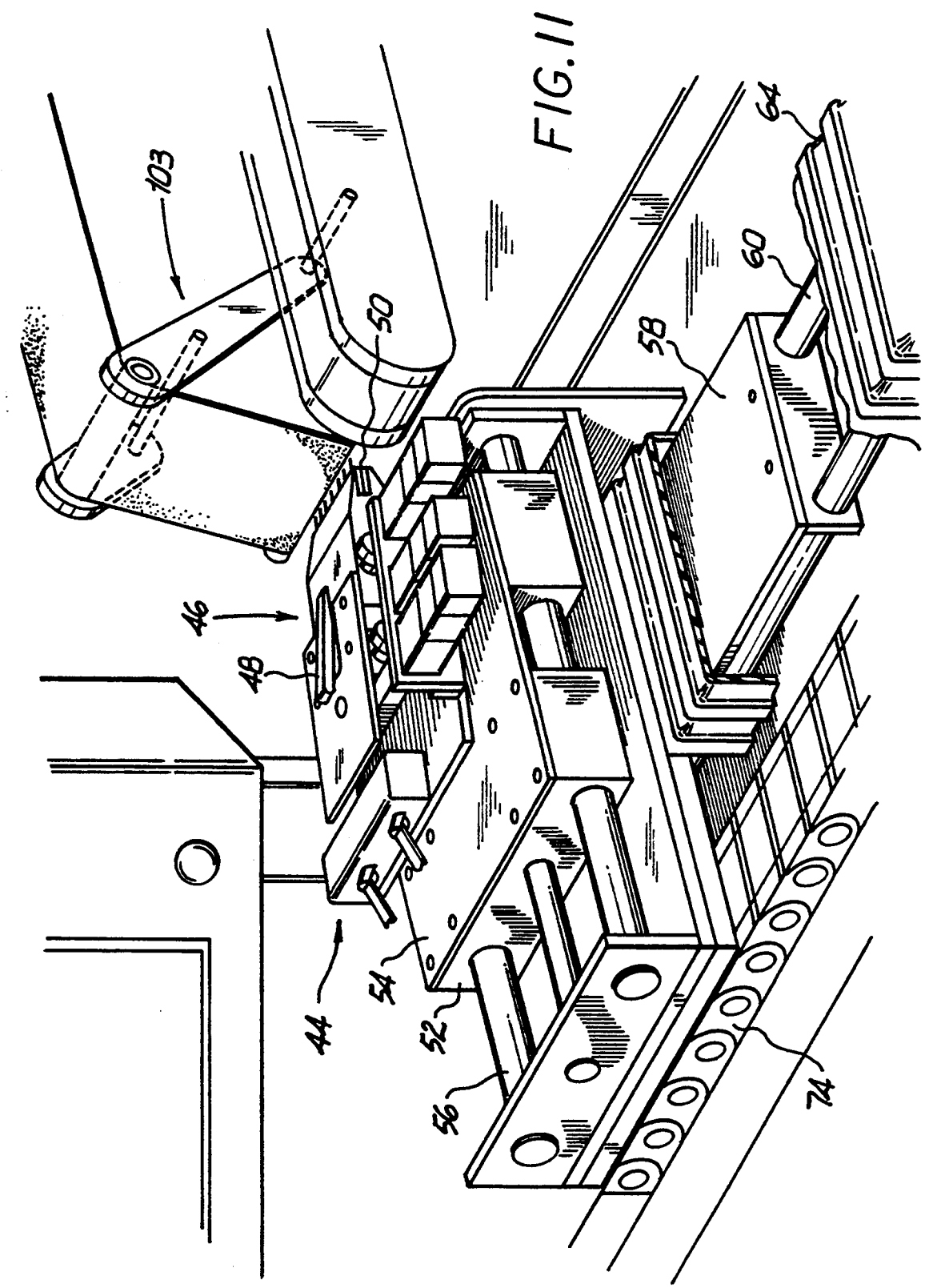

APPARATUS FOR APPLYING A CUTTING EDGE TO A NEEDLE

BACKGROUND OF THE INVENTION

1. Field of the Invention

The present invention relates to devices for preparing surgical needles, and more particularly to devices for abrading the needle to provide a surgical cutting edge on the needle through the use of an abrasive surface for grinding and/or polishing a needle, or a multiplicity of needles, simultaneously.

2. Description of the Related Art

Surgical needle manufacture is a precise and time consuming procedure, particularly where individual needles are formed one at a time. Conventional surgical needle manufacturing typically begins with the step of cutting round wire stock to a predetermined length to form a needle blank. One end of the blank is then tapered to provide a point thereon. In some instances, such as for example in plastic surgery needles or taper cutting edge needles, a cutting edge must be formed at or near the point of the needle. To provide a cutting edge, the tapered end of the needle is stamped or pressed and then subjected to grinding and/or polishing to sharpen its longitudinal edges. Normally, at least a portion of the needle blank is pressed to provide flat surfaces on a portion of the needle to facilitate grinding. After the cutting edge is formed on the needle, the needle blank is cut to its final desired length and then prepared for suture attachment. The needle may be further subjected to additional steps such as polishing or hardening.

Conventional needle processing is in large part a manual operation. Providing a cutting edge, for example, typically includes the steps of: grasping and holding a needle using a hand held device; manually moving the needle into contact with a rotating abrasive belt or grinding wheel; visually evaluating and/or confirming the progress of needle cutting edge formation; and repeating the steps of manually contacting the needle with abrasive surface and visually checking the progress of the cutting edge formation for each edge to be applied to the needle. Since visual confirmation of a specified cutting edge in the view of the person performing the operation is required, the reproducibility, accuracy and hence quality of the cutting edge is largely a function of the skill and experience of the operator.

More specifically, in the prior art the needle may be held by a pliers-like device or a chuck which grips an end of the needle opposite from the end of the needle where the cutting edge is to be applied. Usually, no more than two needles can be held in the device at one time, and the pliers-like device or chuck is used to manually engage the needle end with a rotating abrasive belt. The end of the needle is maintained in contact with the abrasive belt until the desired cutting edge is fashioned.

One disadvantage to conventional needle abrading devices is that manually positioning needles for abrading can be irregular and inefficient. Additionally, the engagement and extent of the needle processing is visually monitored which can result in an inconsistent needle cutting edge. Another disadvantage of the conventional methods is the reliance on visual affirmation of the needle cutting edge which can be ineffective for meeting precise surgical needle specifications. Finally, the prior art devices provide for substantially little or no automation so that the process is time consuming.

The novel device for applying a cutting edge to a surgical needle obviates the disadvantages encountered in the prior art and provides a device for automatically processing a plurality of needles at the same time. The device provides consistent and reproducible results, particularly with respect to needle geometry and surface finish, which ensures precision and accuracy in the application of cutting edges to needles during large scale manufacture. The device provides for both grinding the cutting edges onto the needle, as well as polishing and deburring to produce the finished product. The device also permits the application of cutting edges on several sides of the surgical needle without necessitating the removal and repositioning of the needles in the device to result in a precision multi-sided cutting edge surgical needle.

SUMMARY OF THE INVENTION

An apparatus for applying a cutting edge to surgical needles is provided which includes a frame for mounting at least one device for abrading the needles and a needle holding mechanism for securing the needles and moving the needles into engagement with the abrading device. The abrading device and the needle holding mechanism are positioned on the frame such that needles can be processed in an automated and efficient manner. The needle holding mechanism may hold a plurality of needle blanks to simultaneously engage the blanks with the abrading devices to provide a substantially identical cutting edge on each of the blanks. It is further contemplated that the needle holding mechanism is capable of rotating the needles to consecutively engage various sides of the needle to provide a multi-sided cutting edge.

The abrading device preferably comprises a motor driven rotatable abrasive member, which rotates the abrasive member at a predetermined speed. The needle holding mechanism is movably mounted to the frame and is selectively positionable in relation to the abrading device. Preferably, the apparatus may provide a plurality of needle abrading devices positioned on the frame, each including at least one rotatable abrasive belt.

The needle holding mechanism selectively engages the needles with the abrasive belts at each of the needle abrading devices. The holding mechanism moves the needles into and out of engagement with the abrasive belts of the abrading devices. The needle holding mechanism transports the needles to a position substantially perpendicular each abrading device.

The needles are engagable with the abrasive belt of each of the abrading devices at predeterminable selectable time intervals. The motion of the needle holding mechanism is hydraulically activated in conjunction with a programmable logic controller which automates the entire process. Hydraulic cylinders move the needles in the needle holding mechanism toward and away from the belt at each abrading device to engage an end of each needle with the belt. Hydraulic cylinders also move the needle holding mechanism to move the needles along an axis parallel to the abrading devices so that the needles can be positioned adjacent to each abrasive belt to be engaged with that belt.

BRIEF DESCRIPTION OF THE DRAWINGS

The foregoing features of the present invention will become more readily apparent and will be understood by referring to the following detailed description of preferred embodiments of the invention, which are described hereinbelow with reference to the drawings wherein:

FIGS. 7A, 7B and 8 are perspective views illustrating stock needles prior to the application of a cutting edge;

FIG. 9 is a perspective view illustrating a needle having a cutting edge applied thereon;

FIG. 10 is a cross-sectional view of the cutting edge of the needle shown in FIG. 9 taken along lines 10—10; and FIG. 11 is a perspective view illustrating an alternate embodiment of the apparatus of the present invention.

DETAILED DESCRIPTION OF PREFERRED EMBODIMENTS

Figure 1:
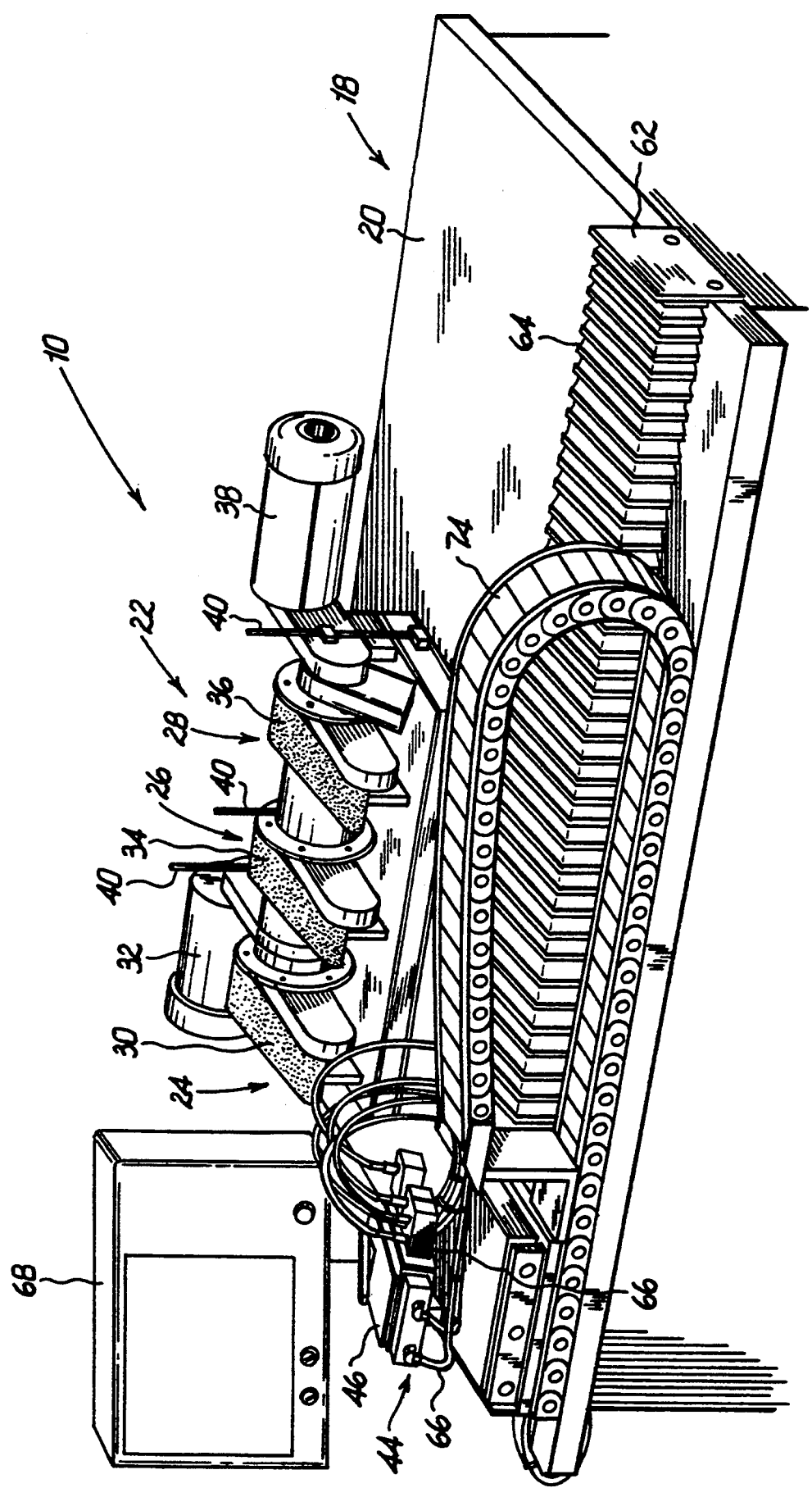
FIG. 1 is a perspective view illustrating an apparatus for applying a cutting edge to a needle according to the present invention.

Referring to the drawings, in which like reference numerals identify identical or similar elements, there is illustrated a preferred embodiment of an apparatus 10 for applying a cutting edge to surgical needles. Apparatus 10 processes stock needle blanks, such as blank 12, 12' shown in FIGS. 7A and 7B, respectively, or a pre-tapered blank 14 as shown in FIG. 8. A portion of the needle blank may be coined or flat pressed to impart a desired cross-sectional shape to the needle blank prior to processing by apparatus 10. Apparatus 10 applies at least one cutting edge 16 on blank 12, and in a preferred embodiment, three edges 16 are applied as seen in FIGS. 9 and 10.

Figure 2:
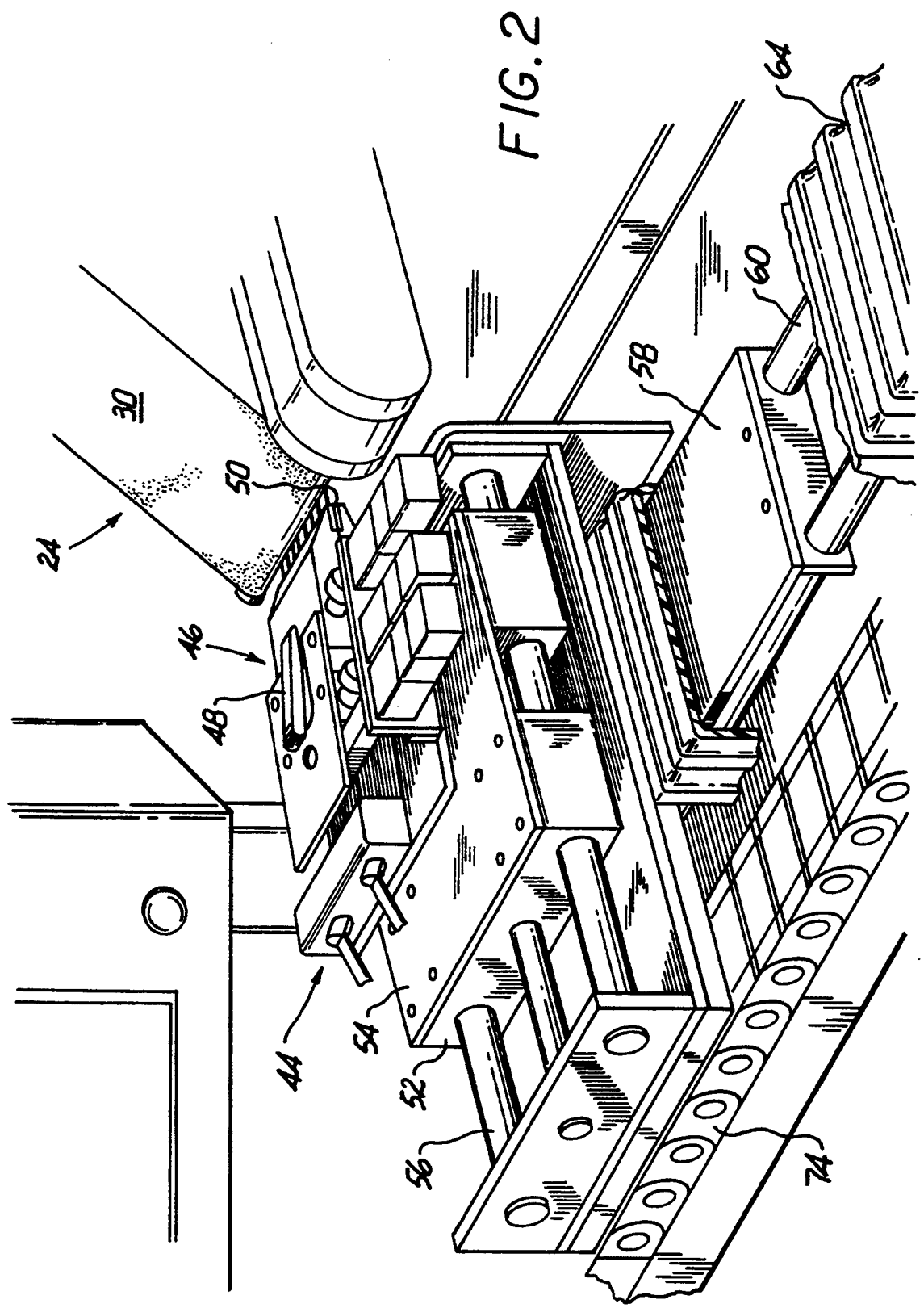
FIG. 2 is an enlarged perspective view illustrating the needle holding mechanism of the apparatus shown in FIG. 1.

Referring to FIGS. 1 and 2, the apparatus 10 includes a frame or table 18 having a working surface 20. The apparatus 10 comprises a series of abrading stations 22 positioned on the work surface 20 for abrading a multiplicity of needles to apply cutting edges thereon. The abrading stations 22 refine the needle blank 12 in sequential stages using rotating abrasive devices such as grinding belts or grinding stones and wheels. Each abrading device of the station 22 preferably represents a predetermined stage of needle refinement.

The present invention processes a needle blank 12 to result in three cutting edges 16 utilizing three separate abrading devices 24, 26 and 28. Alternative embodiments, however, may have more or less than three abrading devices, and further may provide cutting edges on more or less than three sides.

As best seen in FIGS. 1 and 3–5, the first abrading device 24 includes a first rotatable abrasive belt 30 rotated at a desirable speed by a motor 32. The first abrasive belt 30 fashions a cutting edge on a needle by grinding an end of the needle blank 12. The first belt 30 has an abrasiveness for grinding an initial cutting edge on the end of a needle blank 12.

A second abrading device 26 is positioned laterally adjacent and along a common axis with the first abrading device 24. The second abrading device 26 includes a second rotatable abrasive belt 34 for further abrading blank 12 to apply the cutting edge on the needle blank 12.

The second belt 34 can also be rotated by motor 28. Preferably, however, another motor is used to rotate second belt 34 to allow a different grinding speed in connection with second belt 34. Different grinding speeds may be desirable for belts containing different abrasives, depending on factors such as abrasive composition or grit size. The second abrasive belt 34, preferably, is less abrasive than the first belt 30 to further refine the cutting edge after engagement with the first abrasive belt 30. In another embodiment, it is also contemplated that the second abrasive belt 34 could be equally or more abrasive than the first belt.

A third abrading device 28 is positioned laterally adjacent to and along a common axis with the first two abrading devices 24 and 26. The third abrading device 28 includes a third rotatable abrasive belt 36 rotated by motor 38 at a predetermined speed. Preferably, the abrasiveness of the third belt 36 is less than the abrasiveness of the second abrasive belt 34, and is particularly adapted for polishing the needle cutting edge 16 to deburr the edge applied by the first two abrading devices 24 and 26. The third belt 36 may comprise a velvet flock belt to provide for deburring and polishing. However, deburring may also be accomplished by reversing the direction of third belt 36. Also, the speed of the motor 38 may be adjusted for optimum polishing of the cutting edge.

Figure 3:
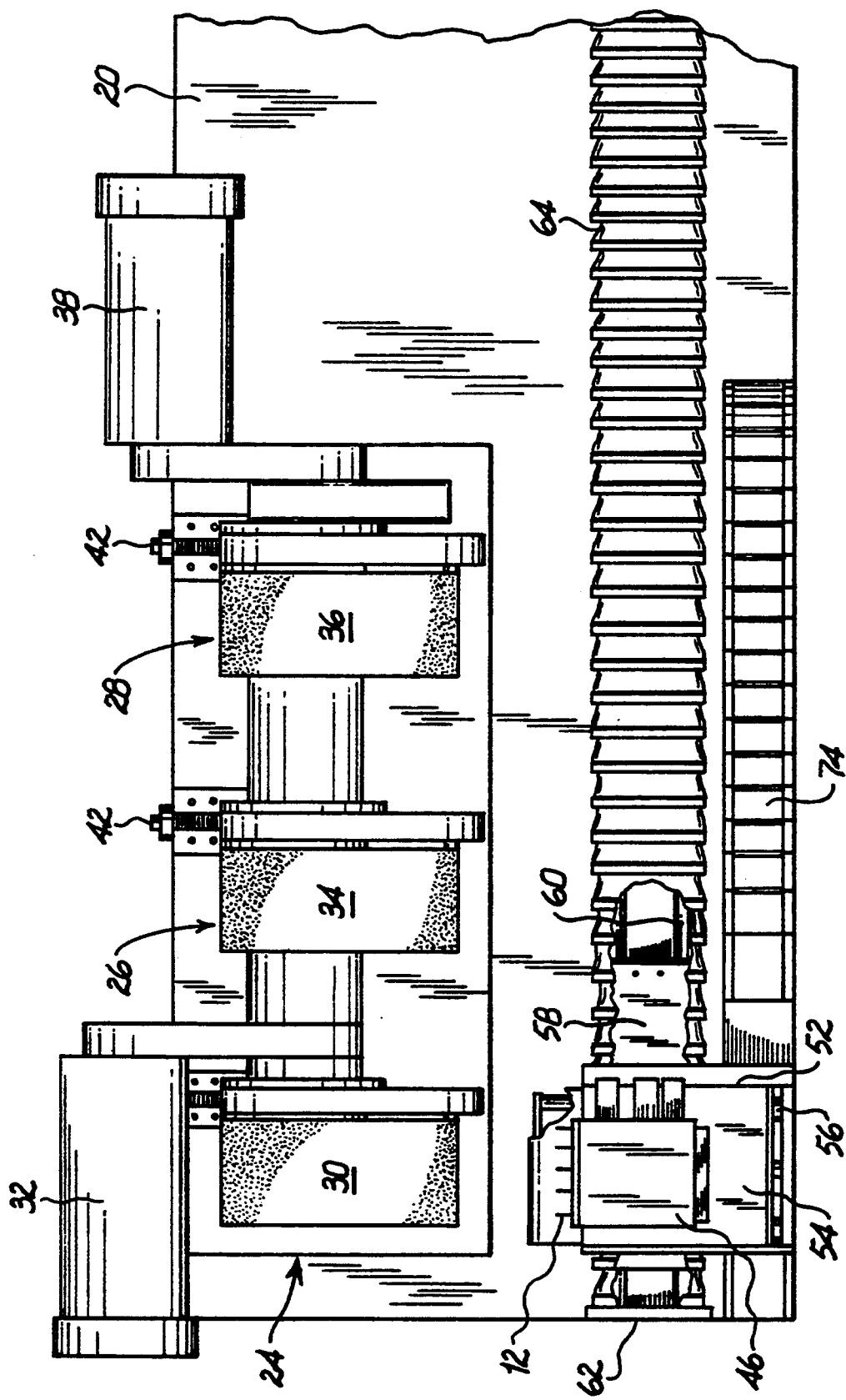
FIGS. 3–5 are top plan views illustrating a needle processing sequence using the apparatus of FIG. 1.
Figure 4:
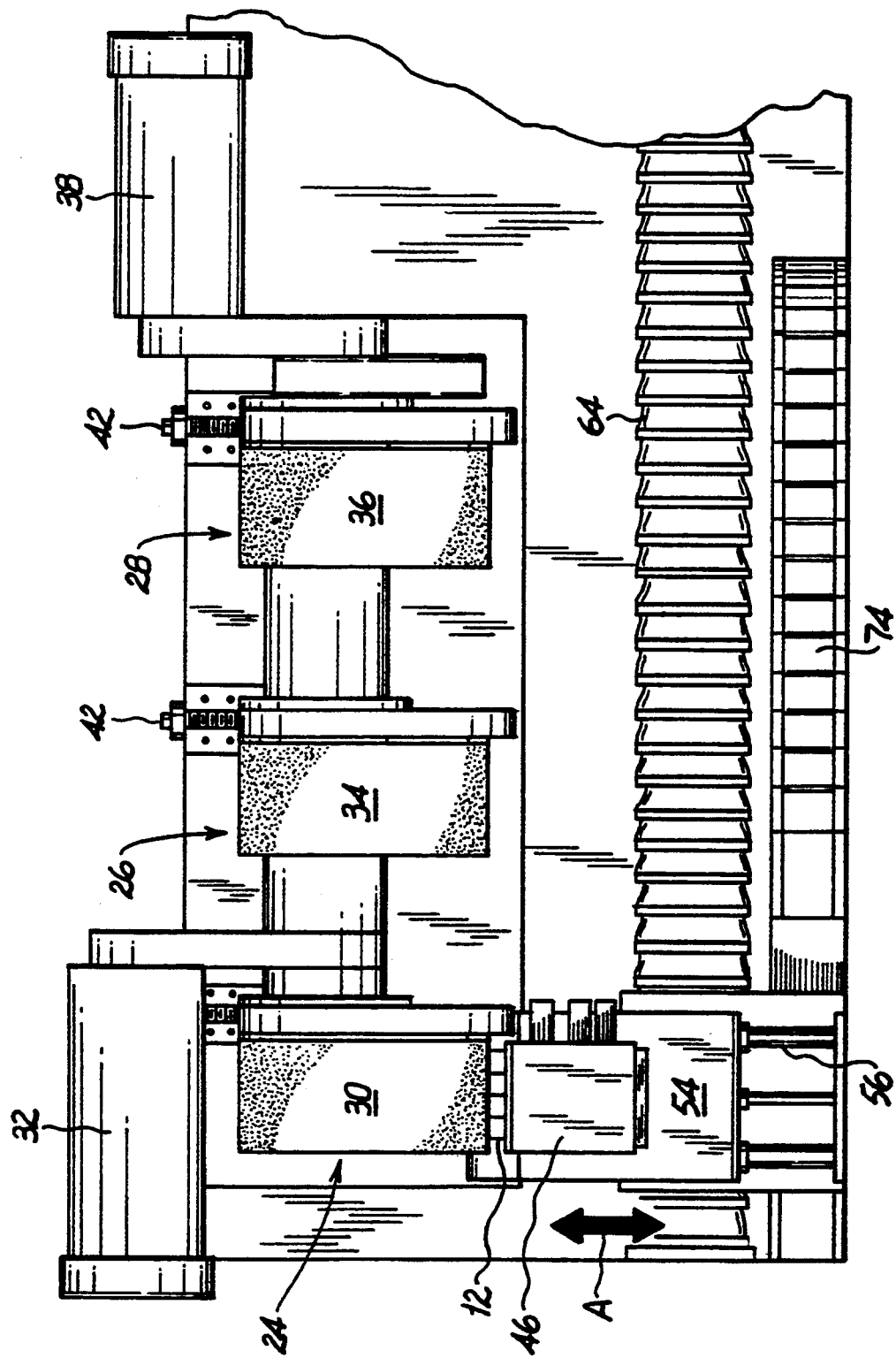
Figure 5:
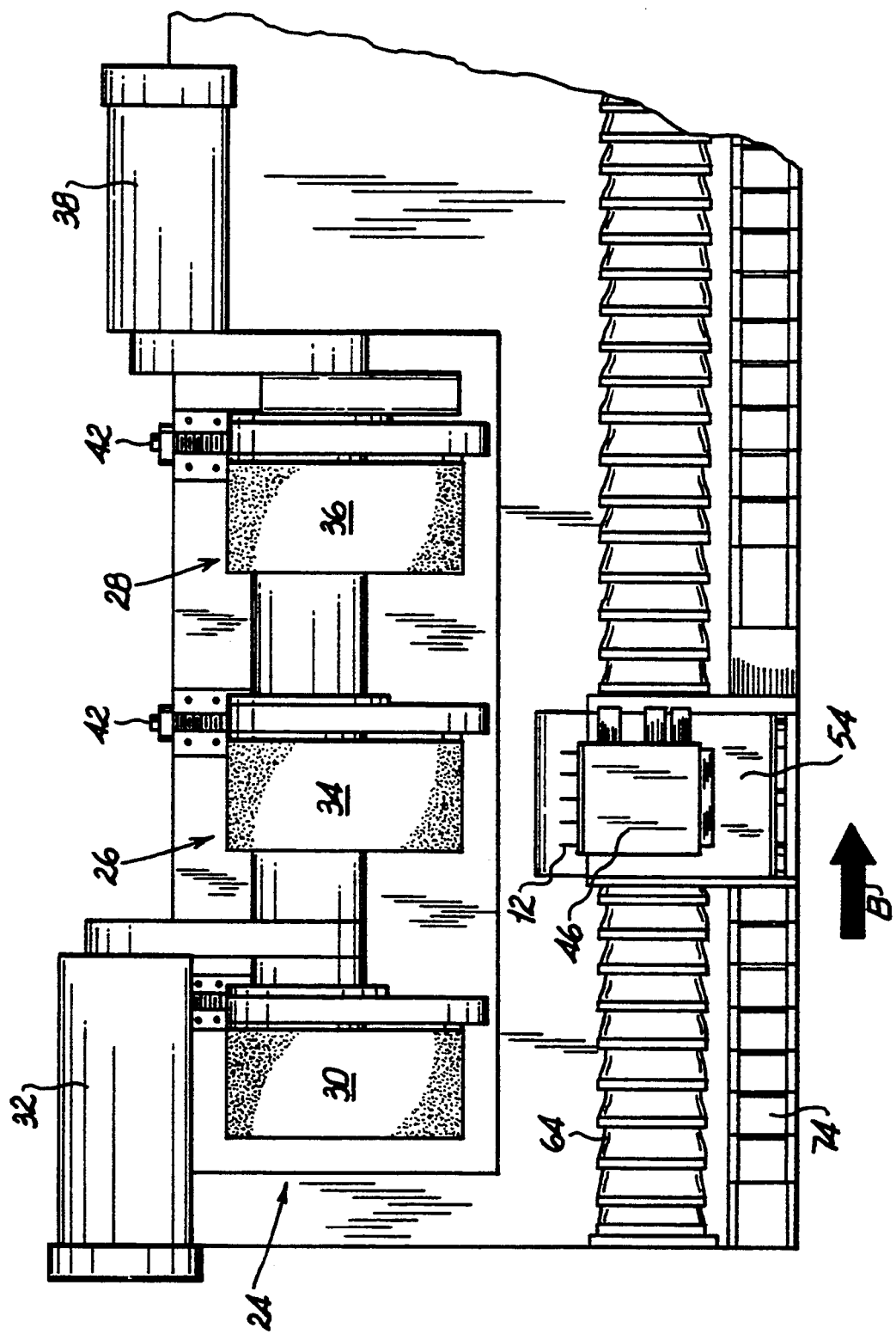

As seen in FIG. 1, the angle of the belts in relation to the needle blanks may be varied by adjusting the height of the abrading devices 24, 26 and 28 utilizing adjusting rods 40. In addition, as best seen in FIGS. 3–5, the distance between the belts and the rest position of the needle clamp 46 may be regulated by adjusting knobs 42 to advance or retract the belts. In an alternative embodiment the tension on the belts may be adjusted using mechanism 103 shown in FIG. 11.

The abrasive belt at each of the abrading devices 24, 26 and 28 each preferably have an abrasiveness having micron values of between about 0.3 microns to about 100 microns. While abrasive belts are preferred, it is also contemplated that abrasive wheels and grinding wheels may also be employed.

While the preferred embodiment utilizes three abrading devices, it is also contemplated that an alternative apparatus may include any number of abrading devices for fashioning a cutting edge on a needle blank instead of a series of processing stations. The envisioned alternative apparatus may include a variable speed motor for rotating an abrasive belt at different speeds. Further, a series of belts can be interchangeably fitted on a rotating structure to provide various abrasive surfaces.

Figure 6:
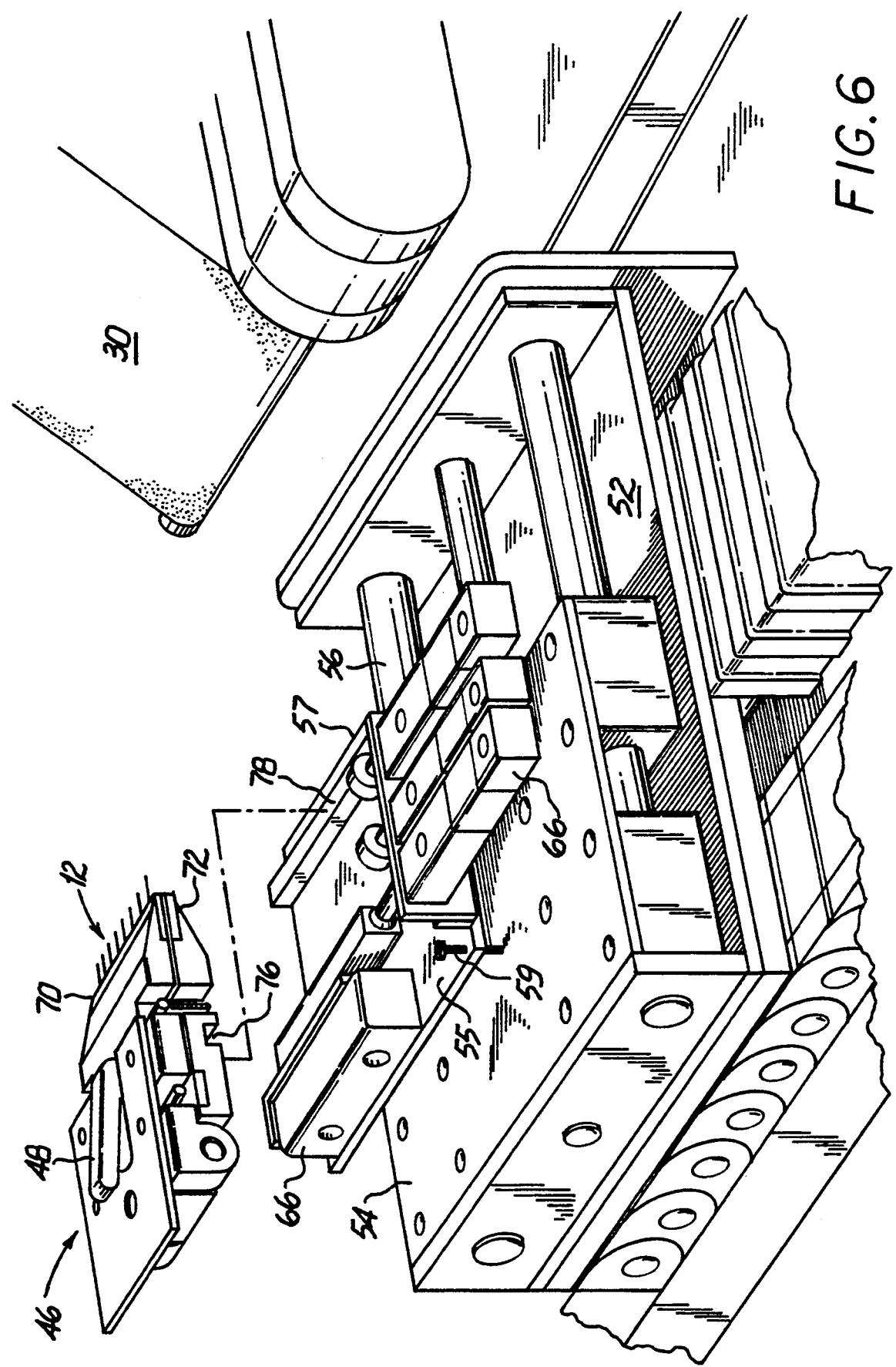
FIG. 6 is an enlarged perspective view of the apparatus of FIG. 2 with the needle holding mechanism in an exploded view.

Referring now to FIG. 2, a needle holding mechanism 44 is shown which includes a needle clamp 46 dimensioned and configured to hold at least one needle blank 12, or a multiplicity of needles 12 as shown. The needles 12 are releasably held in the clamp 46, which may be disengaged as seen in FIG. 6 to remove the needles 12 from the clamp 46. This is accomplished by moving lever 48 upwardly to open the jaws 50 of the needle clamp 46.

The needle holding mechanism 44 comprises an upper rod carriage 52 having a mounting block 54 for positioning the needle clamp 46 thereon. The mounting block 54 is slidably positioned on upper rods 56 connected to the upper rod carriage 52. The mounting block 54 slides along upper rods 56 in a substantially perpendicular direction from the abrading stations 22. Thus, the mounting block can be moved towards and away from the abrading devices 24, 26 and 28 in a smooth manner. The upper rod carriage 52 may also be moved parallel to the abrading stations 22 through the provision of a lower rod carriage 58. The lower rod carriage 58 and the upper rod carriage 52 are mounted to each other in overlapping relation. As the lower rod carriage 58 moves along an axis parallel to the abrading stations 22, it carries the upper rod carriage 52, as well as mounting block 54 and clamp 46.

The lower rod carriage 58 is slidably connected to a series of lower rods 60. The lower rods 60 are secured to plates 62 (see FIGS. 1 and 5) on the frame 18 and extend along an axis parallel to the abrading stations 22. Thus, as the lower rod carriage 58 moves along the lower rods 60, the lower rod carriage 58 moves parallel to the abrading devices 24, 26 and 28. The upper rod carriage 52, attached to the lower rod carriage 58, moves in concert with the lower rod carriage 58. The upper rod carriage 52 can thus be positioned adjacent to each of the belts of the abrading devices 24, 26 and 28.

At some point, due to the length of rods 60, there may be some downward deflection of rods 60 as the carriages 52, 58 move therealong. In such instances rather than rods, a linear way is substituted therefore. The linear way includes a track mounted directly to surface 20 to avoid the possibility of downward deflection. The lower carriage 58 rides in longitudinal channels formed in the track and is provided with guides on its underside which provide smooth movement of the carriage along the track.

The lower rod carriage 58 is protected from debris during the abrading process by a cover 64. Preferably, the cover 64 is flexible and has an accordion-like appearance. The cover 64 discourages debris such as metal shavings and the like discharged from the abrading stations 22 from collecting on the lower rods 60 and interfering with the movement of the lower rod carriage 58 along the lower rods 60. The cover 64 shrouds the full length of the lower rods 60 as seen in FIG. 1. As the rod carriages 52 and 58 are moved laterally, the cover 64 flexibly moves with the rod carriages 52 and 58 compressing and expanding appropriately.

As best seen in FIGS. 3-5, mounting block 54 extends almost directly under the needles 12 to cover the front portion of the upper rod carriage 52. Mounting block 54 discourages debris from collecting on the front portion of the upper rod carriage 52 and interfering with carriage 52 during positioning along rods 56.

The needle clamp 46 is provided to hold one or a multiplicity of needles during engagement with the belt at each abrading station 22. A suitable needle clamp is that disclosed in copending U.S. application entitled NEEDLE TRANSPORTING APPARATUS, filed Oct. 9, 1992 under Express Mail Label No. TB115786737US, the disclosure of which is incorporated herein by reference. Hydraulic cylinders 66 are provided and are operably connected to the upper and lower rod carriages 52 and 58. Needles 12 are held in the needle clamp 46 and engage the belts at each abrading device 24, 26 and 28 in a controlled manner. Hydraulic cylinders 66 control the movement of upper and lower rod carriages 52 and 58 and the needle clamp 46 mounted thereon. Hydraulic cylinders 66 respond to instructions provided by an operator through operator interface 68 which sends electrical impulses to a programmable logic controller which activates hydraulic cylinders 66 via known mechanisms. Rod carriages 52 and 58 and the needle clamp 46, are thus capable of selective manipulation as will be described below.

Further, the hydraulic cylinders 66 enable the needles 12 held in needle clamp 46 to be moved toward and away from each belt at predetermined time intervals via upper rods 56. In addition, the speed at which the needles are moved toward each belt, i.e., the plunge speed, can be controlled as desired. Where coarser abrasive belts are used, a quick plunge speed may be desired to control the amount of material removed from the needle and to avoid excessive heat build up. When the needles are being plunged into a polishing belt, a relatively slower plunge rate may be utilized since for the removal of scratches a slower plunge speed is preferred. The controlled movement of the upper rod carriage 52 along the upper rods 56 enables the needles 12 to engage and disengage each belt for a short or long period of time, as well as, repetitive timed intervals if desired. Thus, the controlled and selectable movement of the rod carriages 52 and 58 provides predeterminable grinding and abrading to achieve a specified needle cutting edge.

It is further envisioned that other methods of moving the rod carriages 52 and 58 may be used other than hydraulic cylinder 66, such as, methods utilizing pneumatics, servo-motors, and the like.

Further, the hydraulic cylinders 66 can be used to manipulate the needles 12 held in the needle clamp 46. Specifically, the needles 12 can be rotated while being held in the needle clamp 46. The needle clamp 46 includes a movable jaw 70 and a stationary jaw 72, as best seen in FIG. 6. Manipulation of the movable jaw 70 laterally with respect to the stationary jaw 72 rotates the needles 12 therebetween, to apply cutting edges 16 to various sides of needle 12.

The hoses leading to cylinders 66 are preferably positioned within a flexible articulated receptacle 74. The receptacle 74 is a linked housing which is positioned on the working surface 20 in an overlapped or folded manner and folds and unfolds as the needle holding mechanism 44 and clamp 46 are moved laterally along lower rods 60.

In operation, referring to FIGS. 3-5, the needles 12 held in the needle clamp 46 are positioned in an initial position substantially perpendicular to the first abrasive belt 30 of the first processing station 24, as shown in FIG. 3. The needle clamp 46 is placed on plate 55 and moved via upper carriage 52 on upper rods 56 in the direction of Arrow "A" as seen in FIG. 4, to a position tangential to the first belt 30 to engage the needles 12 with the first belt 30 for a selectable time interval or dwell period. In general, the needle clamp 46 preferably engages the needles 12 with belt 30 for about 100 millisecond to about 30 seconds.

The planar orientation of plate 55 can be adjusted by screw 59 thereby altering the attitude of the needles as they are presented to the belts. By turning screw 59 in one direction, plate 55 pivots upward about an axis defined by front edge 57 of plate 55 as the lower end of screw 59 contacts mounting block 54. Reversing the direction in which screw 59 is turned, plate 55 can be lowered. The planar orientation of plate 55 can preferably be adjusted in a range from 30° above the horizontal to 30° below the horizontal. It is also contemplated that the planar orientation of plate 55 can vary in a predetermined manner as the upper carriage 52 moves toward the belt whereby the needles engage the belt at various angles during the plunge into the belt.

Following grinding the needles 12 with the first belt 30, the needles 12 may be moved away from belt 30, rotated as described above, and then moved to re-contact belt 30. Rotating the needles 12 enables different portions of the needle 12 to be engaged with the belt 30.

After grinding the needles 12 at the first abrading device 24, the needles 12 held in needle clamp 46 are returned to their initial position by moving upper carriage 52 along rods 56 in the direction of Arrow "A" away from belt 30, back to the position shown in FIG. 3. The needles 12 are then moved laterally as seen in FIG. 5 in the direction of Arrow "B" with carriages 52 and 58 via the lower rods 60 to a position substantially perpendicular to the second belt 34 of the second abrading device 26. The needles 12 are then moved towards second belt 34 to be tangentially engaged with the second belt 34 in essentially the same manner as with the previous first abrading device 24 by moving carriage 52 along rods 56 towards belt 34, as indicated above with respect to FIG. 4.

The second belt 34 preferably has an abrasiveness less than that of the first belt 30. Second belt 34 engages the incomplete cutting edge 16 of the needles 12 to further refine the cutting edge. Further, the length and frequency of the time intervals of needle engagement with the second belt 34 may be adjusted in relation to those used with the first belt 30 for attaining optimum processing results. The needles 12 may also be rotated in a similar manner as 5 described previously to further fashion a multi-sided cutting edge.

After grinding of the needles 12 at the second abrading device 26, the needles are returned to their position substantially perpendicular to the second belt 34 so that they can be moved to the third abrading device 28. The needles 12 held in the needle clamp 46 are then moved via the lower rods 60 in a manner similar to that described above, to a position substantially perpendicular to the third belt 36.

At the third abrading device 28, the needles 12 are tangentially engaged with belt 36 in a manner similar to that as disclosed in relation to the two previous abrading devices 24 and 26. However, the third belt 36 is preferably less abrasive than the first two belts 30 and 34 so that the cutting edge of the needles 12 can be deburred and polished. Preferably, belt 36 is a velvet flock belt which refines the cutting edge 16.

After the cutting edges 16 of the needles 12 have engaged the polishing belt 36, the needle clamp 46 is returned to its initial position opposite the first processing station 24, as shown in FIG. 3, via the upper and lower rod carriages 52 and 58.

Referring now to FIG. 6, the needle clamp 46 can then be removed from the mounting block 54. The needle clamp 46 is removably positioned on the mounting block 54, and a groove 76 in the stationary jaw 72 of the needle clamp 46 removably receives mounting bar 78 on mounting block 54.

After the cutting edges 16 of the needles 12 have been applied by apparatus 10, the needle clamp 46 is lifted off the mounting block 54, so that needles can then be removed from the needle clamp 46 by moving the lever 48 upwardly to release the jaws 50 of the clamp 46 which hold the needles 12.

It is envisioned that other means for holding a needle or plurality of needles may be used, such as, a fixed clamp device, or a slotted element for receiving needles.

It is further contemplated that the needle clamp 46 may be moved to desirable positions using other methods than the preferred embodiment described above. For example, slidable plates can be mounted on the lower rod carriage 58 and be used instead of the upper rod carriage 52. The slidable plates may be configured and dimensioned to receive the needle clamp 46 and slide in relation to one another such that the clamp can be moved towards and away from the processing stations.

It is evident from the above described preferred embodiment that various belt speeds and belt abrasiveness may be used, as well as various selectable timed intervals of needle engagement with the belts.

While the invention has been particularly shown, and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. Apparatus for applying a cutting edge to a needle blank comprising:
   means for abrading at least one needle;
   clamp means for holding said needle in contact with said abrading means, said clamp means comprising a first jaw member and a second jaw member, said first jaw member being movable relative to said second jaw member to rotate the needle held by said clamp means; and
   means for moving said clamp means in a direction generally parallel to the axis of elongation of the needle to selectively engage and disengage said needle with said abrading means, said moving means including a controller for automating movement of said clamp means.

2. Apparatus according to claim 1, further comprising means for rotating said abrading means.

3. Apparatus according to claim 2, wherein said abrading means comprises an abrasive belt.

4. Apparatus according to claim 2, wherein said rotating means comprises a motor.

5. Apparatus according to claim 1, further comprising means for deburring and polishing said needle, said positioning means advancing said clamp means from said abrading means to selectively engage and disengage said needle with said deburring means.

6. Apparatus according to claim 5, wherein said deburring means comprises a rotatable flock belt.

7. Apparatus according to claim 5, wherein said positioning means is operable to move said clamp means in at least two directions to move said needle into and out of engagement with said abrading means and said deburring means, and to transport said clamp means between said abrading means and said deburring means.

8. Apparatus according to claim 1, further comprising means for rolling said needle within said clamp means to provide for contact of said needle with said abrading means on various sides of said needle, said rolling means moving said first jaw member in a plane parallel to said second jaw member.

9. Apparatus according to claim 1, wherein said clamp means includes means for moving said first jaw member in a plane perpendicular to said second jaw member to allow for releasing said needle from said clamp.

10. Apparatus according to claim 1, wherein said clamp means is adapted for holding a plurality of needles.

11. Apparatus according to claim 1, wherein said positioning means is hydraulically controlled.

12. Apparatus according to claim 1, further comprising means for adjusting the abrasiveness of said abrading means.

13. Apparatus according to claim 12, wherein said adjusting means includes means for varying the angle at which said abrading means contacts said needles.

14. Apparatus according to claim 12, wherein said adjusting means includes tensioning means for varying the tension on said abrading means.

15. Apparatus according to claim 13, wherein said adjusting means includes means for varying the planar orientation of said clamp means.

16. Apparatus for applying a cutting edge on a needle blank comprising:
at least one abrading device;
at least one polishing device for deburring a needle;
means for holding and rotating at least one needle; and
means for moving said holding means in a direction generally parallel to the axis of elongation of the needle and sequentially positioning said needle holding means in relation to said abrading device and said polishing device, said moving means including a controller for automating movement of said clamp means.

17. Apparatus according to claim 16, wherein said abrading device comprises a rotatable abrasive belt and a motor for driving said abrasive belt.

18. Apparatus according to claim 17, wherein said abrading device includes means for adjusting the angle and tension of said abrasive belt to vary the abrasiveness of said device.

19. Apparatus according to claim 16, wherein said abrading device comprises a plurality of rotatable abrasive belts having differing abrasiveness, and a motor for driving said plurality of belts.

20. Apparatus according to claim 16, wherein said polishing device comprises a rotatable flock belt and a motor for driving said flock belt.

21. Apparatus according to claim 17, wherein said polishing device comprises a rotatable abrasive belt having an abrasiveness less than an abrasiveness of said abrasive belt of said abrading device, and a motor for driving said abrasive belt of said polishing device.

22. Apparatus for applying a cutting edge on a needle blank comprising:
at least one abrading device comprising a rotatable abrasive belt, a motor for driving said abrasive belt and means for adjusting the angle and tension of said abrasive belt to vary the abrasiveness of said device;
at least one polishing device for deburring a needle, said polishing device comprising a rotatable abrasive belt having an abrasiveness less than an abrasiveness of said abrasive belt of said abrading device, and a motor for driving said abrasive belt of said polishing device, said motor of said polishing devices driving said polishing device belt in a direction opposite to said abrasive belt of said abrading device;
means for holding said needle; and
means for sequentially positioning said needle holding means in relation to said abrading device and said polishing device.

23. Apparatus according to claim 16, wherein abrading device and said polishing device are positioned in a common plane.

24. ,Apparatus according to claim 16, wherein said holding means comprises a clamp member having a pair of jaw members, a first jaw member being movable in relation to a second jaw member.

25. Apparatus according to claim 24, wherein said clamp member is releasably mounted to said positioning means.

26. Apparatus according to claim 24, wherein said first jaw member of said clamp member is movable in a direction perpendicular to said second jaw member for releasably holding said needle.

27. Apparatus according to claim 26, wherein said first jaw member of said clamp member is movable in a direction parallel to said second jaw member to rotate said needle with respect to a longitudinal axis of said needle to allow for abrading a plurality of sides of said needle.

28. Apparatus according to claim 27, wherein said clamp member is adapted to hold a plurality of needles.

29. Apparatus according to claim 16 wherein said positioning means moves said holding means in at least two directions.

30. Apparatus according to claim 29, wherein said positioning means moves said holding means in a direction perpendicular to said abrading device and said polishing device, and further moves said holding means in a direction parallel to said abrading device and said polishing device.

31. Apparatus according to claim 16, wherein said positioning means is hydraulically controlled.

32. Apparatus for applying a cutting edge on a needle blank comprising:
at least one abrading device including an abrasive surface rotating in a first direction;
at least one polishing device including an abrasive surface rotating in a second direction which is different than said first direction, said abrasive surface of said polishing device being less abrasive than the abrasive surface of said abrading device;
means for holding at least one needle; and
means for sequentially positioning said holding means in relation to said abrading device and said polishing device.

* * * * *